United States Patent [19]
Martinez de Lahidalga

[11] Patent Number: 6,135,385
[45] Date of Patent: Oct. 24, 2000

[54] SUTURE MATERIAL DISPENSER

[75] Inventor: Hugo Martinez de Lahidalga, Barcelona, Spain

[73] Assignee: B. Braun Surgical, S.A., Barcelona, Spain

[21] Appl. No.: 09/246,712

[22] Filed: Feb. 9, 1999

[51] Int. Cl.[7] .................................................. A61B 17/06
[52] U.S. Cl. ...................................... 242/588.3; 206/63.3
[58] Field of Search ........................... 242/405.1, 405.2, 242/588.3, 588.6, 608.6; 206/63.3, 227, 380

[56] References Cited

U.S. PATENT DOCUMENTS

| | | | |
|---|---|---|---|
| 3,648,949 | 3/1972 | Berger et al. | 242/588.6 X |
| 3,939,969 | 2/1976 | Miller et al. | 206/63.3 |
| 3,972,418 | 8/1976 | Schuler et al. | 206/63.3 |
| 4,961,498 | 10/1990 | Kalinski et al. | 206/63.3 X |
| 5,236,083 | 8/1993 | Sobel et al. | 206/63.3 |
| 5,407,071 | 4/1995 | Lawhon et al. | 242/159 X |
| 5,575,382 | 11/1996 | Sobel et al. | 206/63.3 |
| 5,655,652 | 8/1997 | Sobel et al. | 206/63.3 |
| 5,667,155 | 9/1997 | Cerwin et al. | |
| 5,833,055 | 11/1998 | Cerwin et al. | 206/63.3 |

*Primary Examiner*—Katherine A. Matecki
*Assistant Examiner*—Collin A. Webb
*Attorney, Agent, or Firm*—Diller, Ramik & Wight, PC

[57] ABSTRACT

The suture material dispenser comprises two panels (11, 12) of flexible hard sheet material, engaging each other with deformations (15, 18) and being fixed on top of each other. The panels (11, 12) have rim strips (13, 17) diverging to the outside and forming a channel (20) in the form of a wedge. By turning the panels (11, 12) around the central axis (20), a suture material thread (23) is wound into the channel (20). This thread (23) gets through the slot (21) at the bottom of the channel (20) into a receiving space (22). By pulling at a needle provided at an end of the thread (23), the coil is drawn out of the receiving space (22).

8 Claims, 4 Drawing Sheets

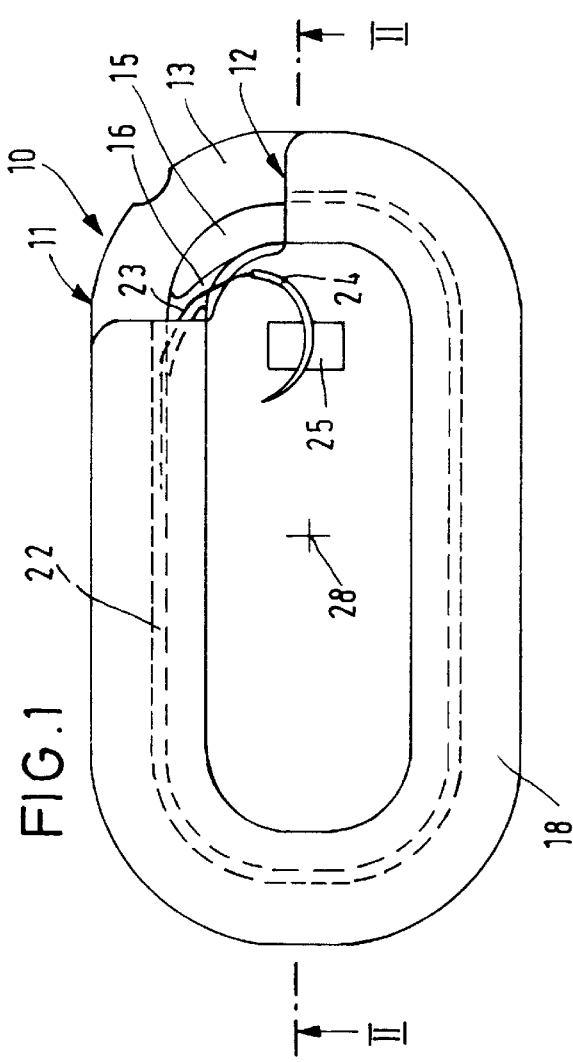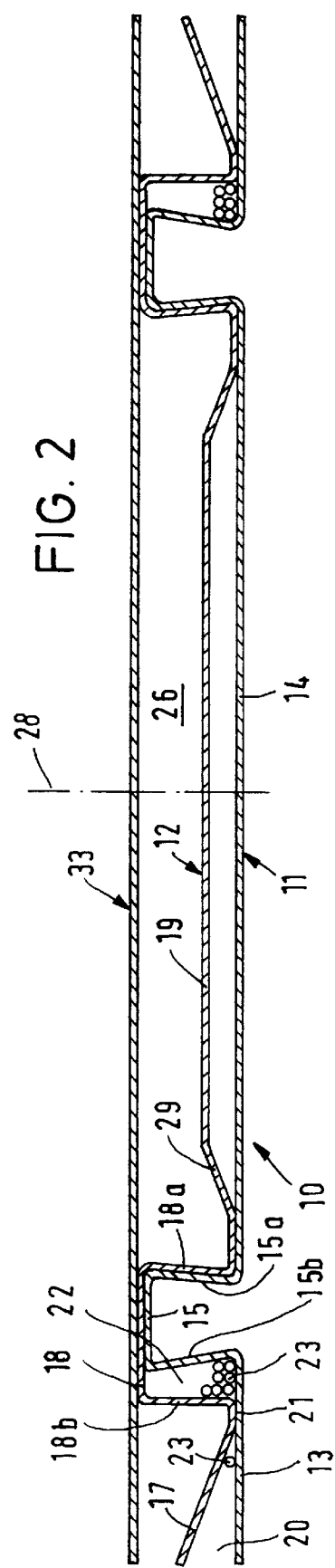

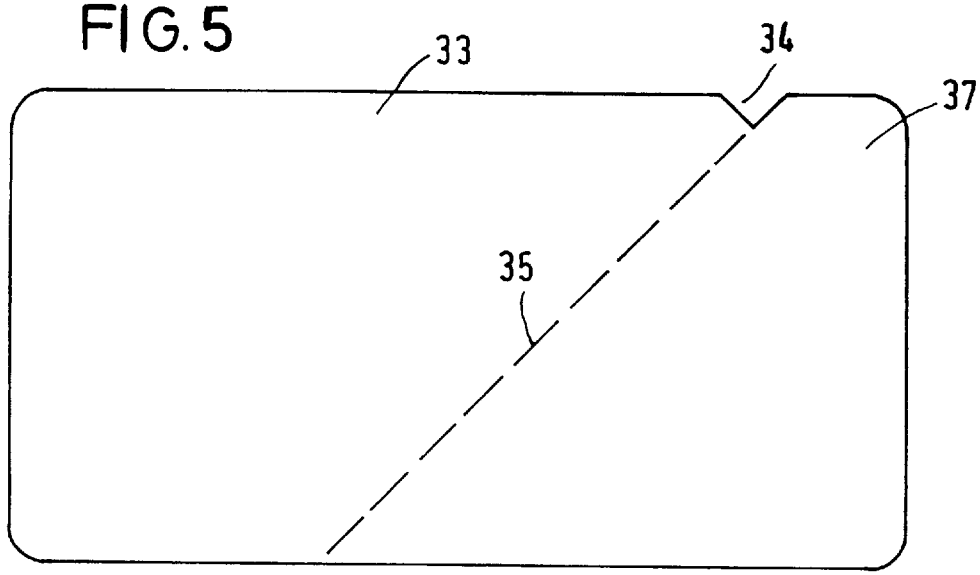
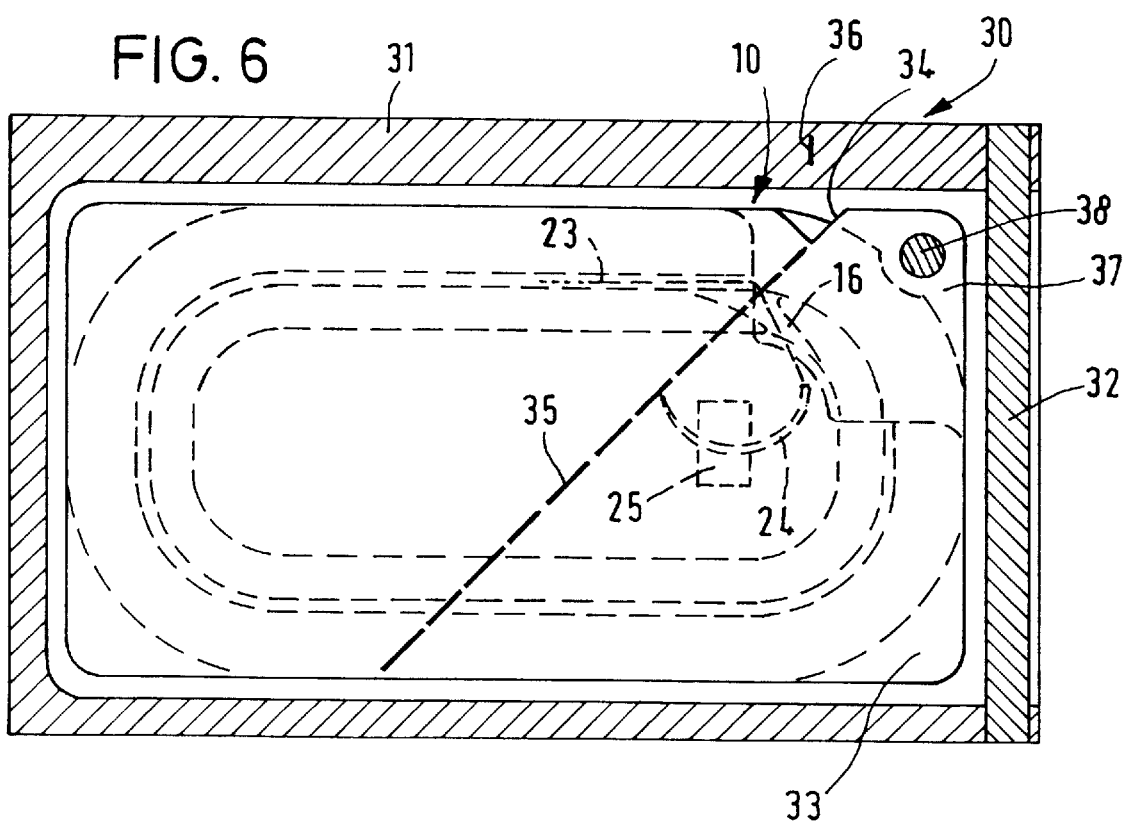

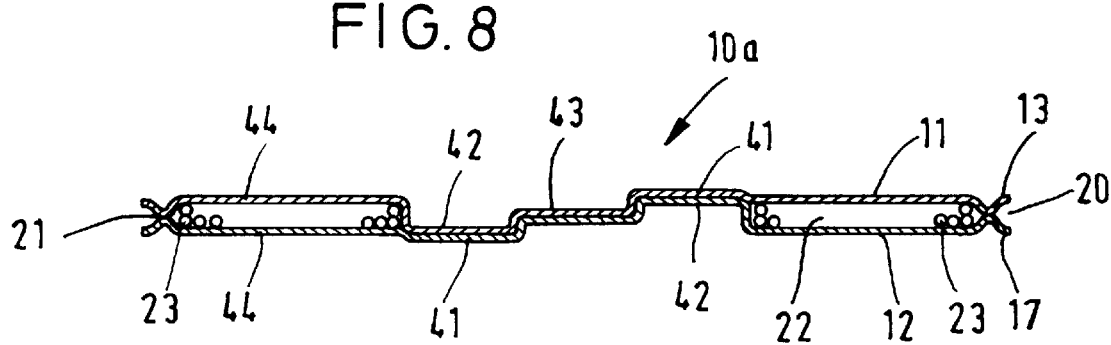
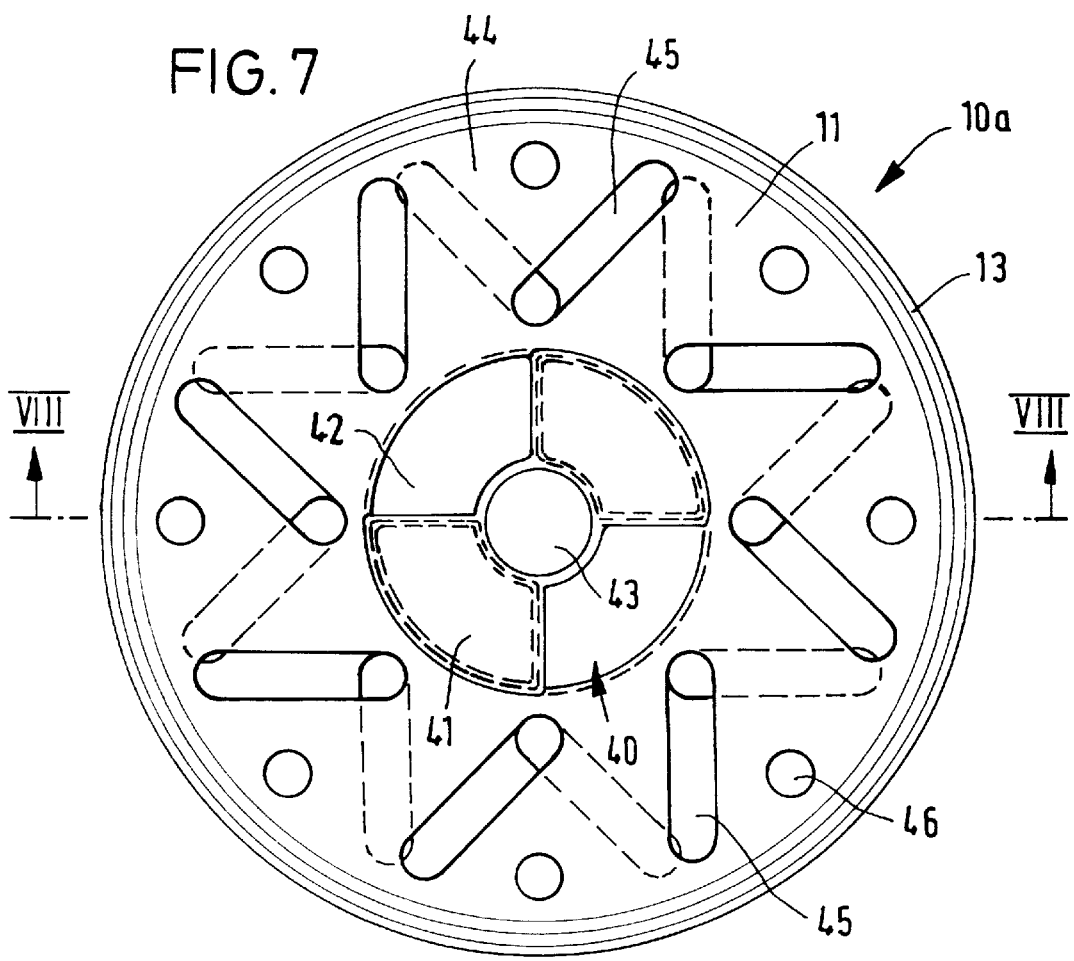

SUTURE MATERIAL DISPENSER

BACKGROUND OF THE INVENTION

The invention refers to a suture material dispenser for surgical suture material and especially, but not exclusively, to a dispenser for needle-thread combinations which are wound around a carrier and can easily be withdrawn from the carrier.

From U.S. Pat. No. 5,667,155, a surgical suture material dispenser is known comprising two parallel panels being fixed to each other. On the upper side of one of these panels, the needle of a needle-thread combination is fixed, and a thread coil is then produced on a winding core positioned on the panel by rotating the panel and the core in the panel plane. Finally, a second panel is put on top of the thread coil. The thread end can be fixed in a clamping slot of the one panel. In such a suture material dispenser, the individual panels have to be mounted to each other after the coil has been produced. The thread coil is located in the form of a spiral between the panels. The suture material has to be pulled out through a hole provided in one of the panels.

SUMMARY OF THE INVENTION

The invention is based on the objective to provide a suture material dispenser having a simple construction and allowing a very simple coiling process.

The suture material dispenser according to the invention consists of two panels on top of each other comprising projecting rim strips forming a channel open to the outside. The suture material dispenser can rotate in the panel plane with the panels being put together, the suture material being drawn into the channel and forming a coil therein. The suture material is thus wound between the rim strips of the panels as in the case of a thread reel. The panels the suture material dispenser consists of form a winding core and a winding coil at the same time.

It is advantageous if the channel tapers towards the inside and ends in an elastic clamping slot. The channel has the function not only to receive the suture material, but also to hold it in place in the clamping slot. The clamping slot forms a brake in which the suture material is clamped. This is possible because the panels consist of flexible elastic shaped parts.

In a particularly suitable embodiment of the invention, the bottom of the channel borders on a slot guiding to a receiving space enclosed by the panels. If a thread is wound into the channel with tension, this thread opens the slot and gets into the receiving space. In this manner, multiple windings of the thread can be urged into the receiving space during the winding process. The receiving space forms a guiding channel receiving and channeling the thread windings. The thread windings are received between the two panels in a protected manner safe from contamination.

The panels can be fixed to each other by adhesion or in another manner. Preferably, they are fixed to each other by engagement of deformations. This makes it possible simply to press the panels onto each other, the panels interlocking and adhering to each other by the clip effect of the deformations. Preferably, the panels consist of a deep-drawn hard sheet material. Thus, the panels can be produced and assembled into the panel unit in a simple manner at low cost. A cost-effective production is important, as the suture material dispensers are one-way articles which cannot be reused.

The central area of the panel unit enclosed by the rim strips or deformations, can be used to attach a needle park to which the needle of the suture material is fixed. According to a preferred embodiment of the invention, it is provided that the deformations of the two panels are interrupted in one place of the circumference and form a passage for passing through the suture material from the inside of the area enclosed by the deformations, so that the thread of the suture material can leave the central area.

In order to be able to grip the suture material in a defined manner, a needle park is provided which is located in a depression formed by one of the two panels. Such a needle park can consist of a slit in the corresponding panel or of a cushion of foam material fixed on the panel or of thermoformed sections or pins of the panel. In the depression, the needle is contained in a protected manner so that its tip cannot cause any unintentional damage. On the other hand, access to the needle fixed in the depression must be possible, i. e. the depression must be formed such as to be able to be exposed, at least partially.

According to a preferred embodiment of the invention, the panel forming the depression is covered by a third panel closing the depression and comprising a tear-open line. This third panel preferably consists of carton material or another fibrous material. The suture material dispenser with the two panels and the third panel is inserted into a jacket forming a packaging. In order to achieve access to the needle when opening the packaging, the third panel serves as a guiding element for the process of opening.

BRIEF DESCRIPTION OF THE DRAWINGS

There now follows a more detailed description of preferred embodiments of the invention with reference to the drawings.

FIG. 1 shows a top view of a first embodiment of the suture material dispenser, the third panel consisting of cardboard having been omitted, FIG. 2 shows a cross section along line II—II of FIG. 1, but with a third panel lying on top of the two panels, FIG. 5 shows a view of the third panel, FIG. 6 shows a representation of the suture material dispenser contained in a jacket, FIG. 7 shows a top view of a second embodiment of the suture material dispenser and FIG. 8 shows a cross section along line VIII—VIII of FIG. 7.

DESCRIPTION OF THE PREFERRED EMBODIMENTS

Figure 3:
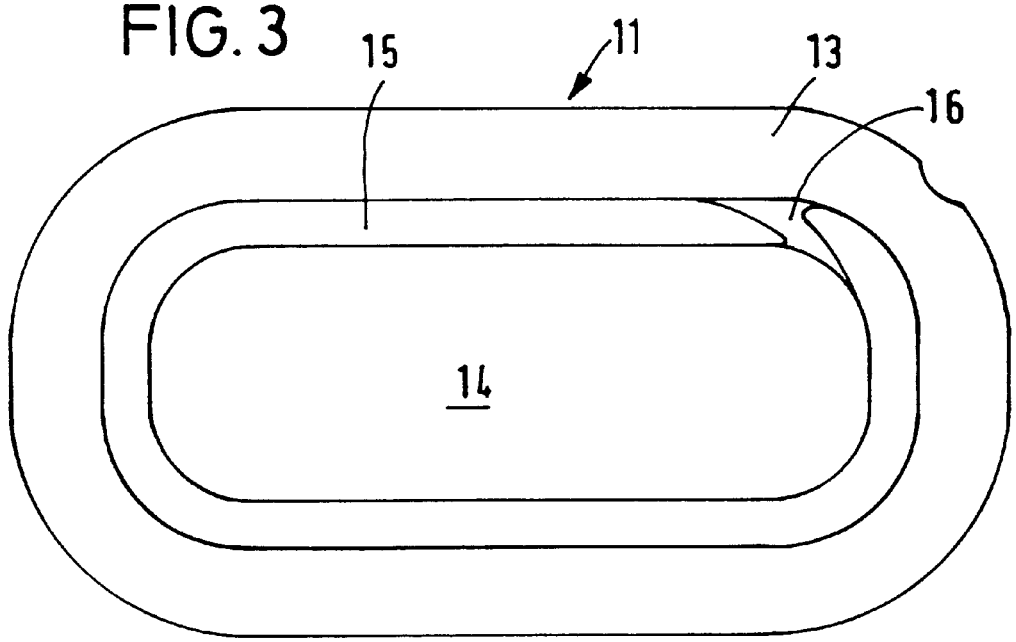
FIG. 3 shows a top view of the lower panel.

The suture material dispenser 10 represented in FIGS. 1 to 6 comprises a lower panel 11 and a substantially congruent upper panel 12 lying on top of the lower panel. Both panels 11, 12 consist of a thermoformed hard sheet material of an appropriate plastic. The panels are dimensionally stable, but elastically deformable. The outer shape of the two panels generally corresponds to an oval or an elongated rectangle with chamfered corners, but any other panel shape is possible in the context of the invention.

The lower panel 11 is provided with a circumferential rim strip 13 extending in the same plane as the central area 14 of this panel. The rim strip 13 encloses a deformation 15 directed upwards extending circumferentially around the central area 14, according to FIG. 3, and comprising an interruption 16 in one place. The deformation 15 forms a base enclosing the area 14. In cross section, the deformation 15 is generally dovetailed. It comprises an interior flank 15a projecting upwards beyond the central area 14 and an exterior flank 15b also projecting upwards beyond the rim strip 13. Thus, the flanks 15a, 15b form undercuts. The upper side of the deformation 15 is planar and extends parallel to the panel plane.

The upper panel 12 also comprises a circumferential rim strip 17, which borders on a circumferential deformation 18 directed upwards having a substantially rectangular cross section. The deformation 18 encloses a central area 19 surrounded by a bevel 29 and thus having a distance from the central area 14 of the lower panel when both panels are on top of each other. The interior flank 18a of the deformation 18 also forms a projection or an undercut, respectively, while the exterior flank 18b extends vertically. The upper wall of the deformation 18 extends horizontally and a really bears against the upper wall of the deformation 15.

The upper panel 12 is pressed on the lower panel 11 such that the interior flank 18a of the deformation 18 is inclined against the interior flank 15a of the deformation 15. When the upper panel 12 is pressed on the lower panel, both panels can be deformed, so that the panels in the mounted state engage each other like a press fastener.

The rim strips 13, 17 projecting outwards form a channel 20 which is open to the outside and has a cross section narrowing to the inside and ending in an elastic clamping slot 21. This clamping slot 21 is formed between the rim strip 17 and the flank 18b of the upper panel 12, in a place where the rim strips 13 and 17 are pressed against each other elastically.

While the inner flanks 15a and 18a of the deformations 15, 18 bear with their faces against each other, the outer flanks 15b and 18b have a distance from each other so that a suture material receiving space 22 is formed between them. This receiving space 22 is produced as the deformation 18 has a greater width than the deformation 15. The receiving space 22 is circumferentially limited by the two panels 11 and 12. It has an access through the clamping slot 21.

The suture material consists of a thread 23 fixed, at one end, to a needle 24. The needle 24 is held by a needle park 25 attached to the upper panel 12, preferably in the depression 26 enclosed by the deformation 18. Starting from the needle 24, the thread 23 is guided through the depression 16 of the deformation 15.

Figure 4:
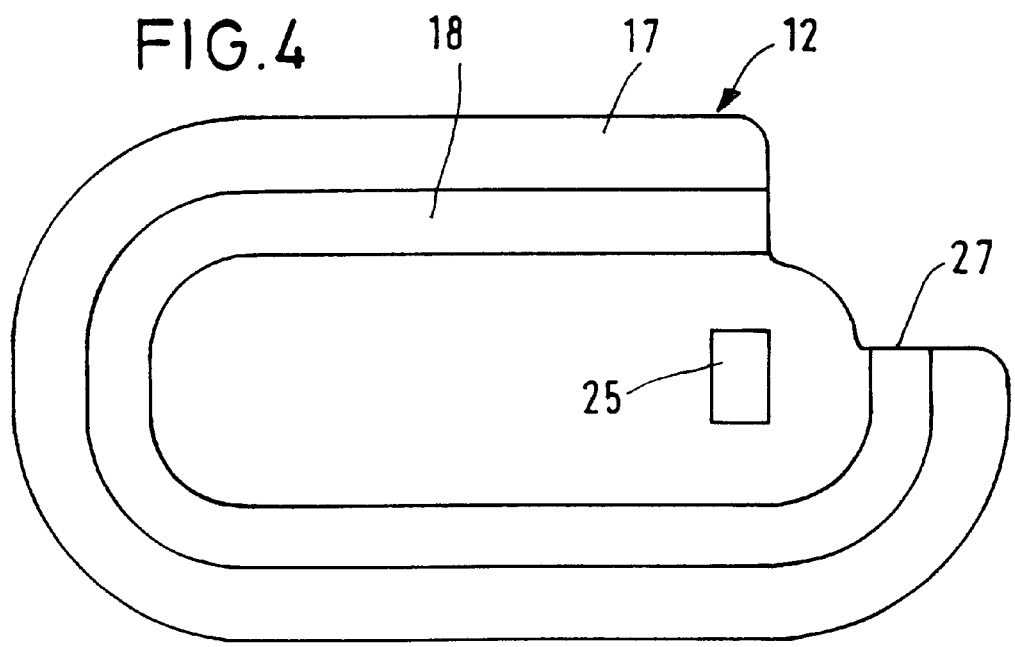
FIG. 4 shows a top view of the upper panel.

As shown in FIGS. 1 and 4, the upper panel 12 has a sector-shaped cutout 27 in the area in which the interruption 26 is located on the lower panel 11, the rim strips 17 and the deformation 18 being cut off in the area of the cutout. That is why the interruption 16 of the deformation 15 of the lower panel is not covered by the upper panel. The thread 23 can thus be guided from the needle park 25 through the interruption 26 to the outside.

Winding the thread 23 occurs by firstly fixing the needle 24 to the needle park 25 and inserting the thread into the interruption 16. After that, the assembly of the two interlocked panels 11, 12 is rotated in a winding machine around its central axis 28. In this, the thread 23 is engaged by the channel 20 and at first received by the channel, as is shown in FIG. 2 on the left side. The thread 23 passes the clamping slot 21 because of the winding tension and gets into the receiving space 22. A flat device provided on the winding machine is used for pressing the thread through the slot 21. In this manner, multiple thread windings can be produced in the receiving space 22, as is shown in FIG. 2. The entire thread coil is finally contained in the receiving space 22 in a protected manner.

In order to take out the suture material, the surgeon grips the needle 24 and detaches it from the needle park 25. When the needle is pulled, the thread 23 is continuously drawn out of the receiving space 22.

Differently from the described embodiment, it is also possible to omit the receiving space 22. In this case, the suture material would be received by the channel 20 or by the clamping slot 21.

The suture material dispenser used for surgical purposes has to be packed in a jacket and sealed from contamination. For this purpose, the jacket 30 consisting of two aluminum sheets is provided. Each aluminum sheet forming the jacket 30 comprises a plastic layer, and the two panels are sealed along welding lines 31 so that a bag is formed into which the suture material dispenser 10 can be inserted. Finally, the opening side is sealed with a sealing seam 32 (FIG. 6).

For opening the jacket 30 in a defined manner for taking out the suture material, the suture material dispenser 10 is covered by a third panel 33 of carton, represented in FIG. 5. This third panel 33 covers the assembly of the first and second panels. It has a substantially rectangular shape and is adapted to the interior space of the jacket 30 so that it fixes the suture material dispenser in the jacket. The third panel 33 is supported on the deformation 18 of the upper panel 12 and can be connected thereto. In the sector lying above the interruption 16, the third panel 33 comprises an indentation 34 from which a slant tear-open line 35 extends through the panel area.

As shown in FIG. 6, the jacket 30 has a tear-open slot 36 at a place adjacent the indentation 34. If the jacket is torn open at the tear-open slot 36, this slot proceeds into the tear-open indentation 34. When the process of tearing open continues, it is guided by the third panel 33 along the tear-open line 35, so that the upper sheet of the jacket tears substantially along the tear-open line 35. Thereby, the needle park 25 holding the needle 24 and the interruption 16 are uncovered. The thread 23 can then be pulled out of the suture material dispenser 10 still located in the jacket 30.

The third panel 33 has a tab 37 extending beyond the two other panels 11, 12 near the tear-open indentation 34 and forming a corner of the third panel. According to FIG. 6, this tab 37 is bonded to the upper sheet of the jacket 30 by an adhesion point 38.

The suture material dispenser can be mounted in a simple manner by pressing the two panels 11 and 12 into each other. Then the winding process takes place in the described manner by rotating the dispenser around its central axis 28 and winding up the thread 23, with the thread 23 getting into the receiving space 22. After that, the two panels 11, 12 are covered by the third panel 33, and the entire panel arrangement is inserted into the jacket 30 and the jacket is closed by producing the sealing seam 32. The jacket 30 can then be inserted into an exterior packaging formed as a peel packaging.

In order to take out the suture material, the jacket 30 is torn open starting at the tear-open slot 36, whereby the suture material becomes accessible.

In FIGS. 7 and 8, a suture material dispenser 10a is represented which is designed to receive at least one suture material thread without needle. Suture material dispensers of this kind are used for veterinary purposes, for example. The suture material dispenser 10a comprises two circular panels 11, 12 of thermo-formed plastic sheet material. The panels 11, 12 holohedrally bear against each other in the central area 40. In the central area 40, four sectors 41, 42 are formed in each panel, the sectors 41 being raised and the sectors 42 being lowered. The panels 11, 12 are turned and set against each other at 90°, the panel 12 being inverted. Thereby, the lowered areas 42 of the one panel are pressed into the raised areas 41 of the other panel. In the central area 43, both panels 11, 12 are at a medium height. By this design it is achieved that the suture material dispenser 10a can be assembled with two identical panels, which are inverted relative to each other and are turned by 90°.

Outside of the central area 40, the panels 11, 12 each have a wall 44 raised relative to the central area 43. The two panels 11, 12 enclose an annular receiving space. The receiving space 22 is limited to the outside by a slot 21 formed by deformation grooves of the panels. The rim strips 13, 17 diverging to the outside border on the slot 21.

The panels 11, 12 are interlocked by pressure fitting in the central area 40. Then the suture material is wound into the channel 20. In this process, the suture material thread 23 passes the slot 21 and gets into the receiving space 22, as is represented in FIG. 8.

According to FIG. 7, slots 45 and holes 47 can be formed in the walls of the panels 11, 12 through which the suture material 23 can be seen from the outside. Apart from that, these holes and slots serve to facilitate the sterilization of the suture material.

What is claimed is:

1. A suture material dispenser comprising one and another panels (11, 12) interlocked together, said panels (11, 12) each including a circumferential rim strip (13, 17, respectively) collectively defining a channel (20) which expands radially outwardly and is adapted to receive therein suture material wound therein, said panels (11, 12) including cooperative engaged deformations (15, 18, respectively) for securing said panels (11, 12) to each other, and said deformations (15, 18) being interrupted at one place of the circumference forming a passage (16) for passing therethrough suture material from the channel (20).

2. The suture material dispenser as defined in claim 1 wherein a bottom of the channel (20) leads to a slot (21) which leads to a space (22) enclosed by the panels (11, 12).

3. The suture material dispenser as defined in claim 1 wherein each of the panels (10, 11) is made of deep-drawn hard sheet material.

4. The suture material dispenser as defined in claim 1 wherein a depression (26) housing a needle park (25) is defined by one of said panels (11, 12).

5. The suture material dispenser as defined in claim 4 wherein one panel (12) is covered by a planar third panel (33) closing the depression (26).

6. The suture material dispenser as defined in claim 4 wherein one panel (12) is covered by a planar third panel (33) closing the depression (26), and said third panel (33) includes a tear-line (35) defining a tear panel.

7. The suture material dispenser as defined in claim 6 including a tab (37) of said tear panel which projects beyond said one and another panels (11, 12) to facilitate tear panel removal.

8. The suture material as defined in claim 7 wherein all said panels (11, 12, 13) are contained in a jacket (30) formed of two sheets sealed along rims thereof, and the jacket (30) is bonded to the tab (37).

* * * * *